(12) United States Patent
Hilgers

(10) Patent No.: US 6,328,965 B1
(45) Date of Patent: *Dec. 11, 2001

(54) VACCINE ADJUVANTS

(75) Inventor: Luuk Hilgers, Utrecht (NL)

(73) Assignee: American Cyanamid Company, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/860,453

(22) PCT Filed: Dec. 21, 1995

(86) PCT No.: PCT/BE95/00119

§ 371 Date: Sep. 15, 1997

§ 102(e) Date: Sep. 15, 1997

(87) PCT Pub. No.: WO96/20008

PCT Pub. Date: Jul. 4, 1996

(30) Foreign Application Priority Data

Dec. 27, 1994 (BE) .................................................... 9401174

(51) Int. Cl.[7] ......................... A61K 39/00; A61K 47/36; A61K 47/40; A61K 47/44

(52) U.S. Cl. .................................. 424/184.1; 424/278.1; 424/283.1

(58) Field of Search .............................. 424/280.1, 278.1, 424/279.1, 283.1, 184.1

(56) References Cited

U.S. PATENT DOCUMENTS 5,976,538 * 11/1999 Hilgers et al. ..................... 424/184.1
6,165,995 * 12/2000 Hilgers .................................. 514/58

FOREIGN PATENT DOCUMENTS

549074 * 6/1993 (EP) .............................. A61K/39/39

OTHER PUBLICATIONS

Hilgers et al. Vaccine 12(7):653–660, May 1994.*

* cited by examiner

Primary Examiner—Mary E. Mosher
(74) Attorney, Agent, or Firm—Adley Mandel; John F. Levis

(57) ABSTRACT

Vaccine adjuvants comprising a sulpholipid polysaccharide in combination with an interface-forming constituent. The invention also provides a method for preparing a vaccine by emulsifying an aqueous solution of an antigen and a sulpholipid polysaccharide. The adjuvants are stable at high temperatures, and are at least as effective as conventional adjuvants. Their local toxicity, i.e. their reactogenicity, is generally lower than that of conventional adjuvants.

33 Claims, No Drawings

VACCINE ADJUVANTS

The present invention relates to novel vaccine adjuvants.

An antigen is defined as a foreign substance for a given organism, which when administered, for example, parenterally, induces an immune response, for example, the formation of antibodies.

Antibodies are substances contained in the blood and other fluids of the body, as well as in the tissues, and which bind to the antigen to make it innocuous. Antibodies constitute one of the natural defense mechanisms of the body. They are highly specific and they can kill, bind or make innocuous the antigen which has induced their formation.

The antigen, in contact with the immune system, thus activates a complex series of cellular interactions to eliminate the antigen and/or to reestablish the preceding equilibrium.

Two of the characteristic features of antigens are their immunogenicity, that is their capacity to induce an immune response in vivo (including the formation of specific antibodies), and their antigenicity, that is their capacity to be selectively recognized by the antibodies whose origins are the antigens.

It is known how to stimulate the immune response deliberately by administrating a specific antigen by means of a vaccine. The procedure allows the obtention of a state of immune response in the organism which allows a more rapid and more effective response of the organism during subsequent contact with the antigen.

However, some antigens have only a weak immunogenicity and they induce an insufficient immune response to procure an effective protection for the organism.

The immunogenicity of an antigen can be increased by administering it in a mixture with substances, called adjuvants, which increase the response against the antigen either by directly acting on the immunological system or by modifying the pharmacokinetic characteristics of the antigen and by thus increasing the interaction time between the latter with the immune system.

At this time, a great number of veterinary vaccines use adjuvants still comprising the standard emulsions of mineral oil, such as the adjuvant of the water in mineral oil type (W/O) or of the mineral oil in water type (O/W). For several years, research studies have been carried out to find alternatives having a similar efficacy at a reduced toxicity. The injections of these standard adjuvants based on mineral oil are often accompanied by local reactions whose severity depends to a large extent on the type of the emulsion and the nature of oil used. The use of adjuvants based on mineral oil is consequently limited to domestic animals (pigs, hens, ruminants, etc.) and laboratory animals.

Earlier, it has been shown that a synthetic copolymer of polysucrose and epichloridrin [sic; epichlorohydrin]—Ficoll—bearing sulfate and lipid groups (SL-Ficoll), incorporated in an emulsion of squalane (S) in water (S/W), had high adjuvant effect on different animal species—including pigs—against different types of antigen, including a few important viral antigens (Vaccine, Vol. 12, pp. 653–660 (1994) and Vaccine, Vol. 12, pp. 661–665 (1994), EPO 0,549,074). These formulations of Ficoll-based adjuvants are sufficiently effective to replace the standard formulations of mineral oil in water used in different porcine vaccines.

However, the local toxicity, that is the reactogenicity of these Ficoll-based formulations in pigs and mice did not turn out to be weaker than that of the standard formulations of mineral oil of the O/W type.

In addition, for the Ficoll-based formulations, the temperature has a pronounced effect on the stability of the emulsions. Some of these emulsions were stable for years at 4° C., but the aqueous phase and the oil phase separate within a few days at 37° C., and within approximately 10 min at 60° C.

The purpose of the present invention is to propose an effective adjuvant for vaccines having an increased stability at high temperature and presenting a lower local toxicity.

This purpose is achieved by an adjuvant for vaccines comprising a sulfolipid polysaccharide combined with an interface-forming constituent (for example, an emulsion of the oil/water type (O/W)).

One of the advantages of the adjuvant according to the present invention is that it is more stable at high temperature than the Ficoll-based adjuvants.

This purpose is achieved by an adjuvant for vaccines comprising a sulfolipid polysaccharide combined with an interface-forming constituent.

The expression "polysaccharide" denotes a compound having at least three repeating sugar units connected covalently to each other.

The expression "sulfolipid polysaccharide" denotes a compound having at least three repeating sugar units connected covalently to each other, at least one sulfate group and at least one lipid group.

Preferably, the sulfolipid polysaccharide is a hydrophobic polysaccharide.

The expression "hydrophobic polysaccharide" denotes a polysaccharide which is less soluble in an aqueous phase than an a polar organic phase.

According to a first advantageous embodiment, the sulfolipid polysaccharide is selected from the group consisting of cyclodextrin, maltodextrin, insulin, Ficoll and Pullulan.

Preferably, the sulfolipid polysaccharide is selected from the group consisting of cyclodextrin, maltodextrin and insulin.

The preferred sulfolipid polysaccharide is cyclodextrin.

The sulfolipid polysaccharide contains, on average, at least 0.01 sulfate group per monosaccharide, while maintaining its hydrophobic character. Preferably, the sulfolipid polysaccharide contains, on average, at least 0.12 sulfate group per monosaccharide, while maintaining its hydrophobic character.

The sulfolipid polysaccharide on average contains not more than 1.0 sulfate group per monosaccharide, while maintaining its hydrophobic character. Preferably, the sulfolipid polysaccharide contains, on average, not more than 0.23 sulfate group per monosaccharide, while maintaining its hydrophobic character.

Preferably, when the sulfolipid polysaccharide is maltodextrin, it contains, on average, approximately 0.23 sulfate group per monosaccharide, while maintaining its hydrophobic character.

Preferably, when the sulfolipid polysaccharide is cyclodextrin, it contains, on average, approximately 0.20 sulfate group per monosaccharide, while maintaining its hydrophobic character.

Preferably, when the sulfolipid polysaccharide is insulin, it contains, on average, approximately 0.19 sulfate group per monosaccharide, while maintaining its hydrophobic character.

Preferably, when the sulfolipid polysaccharide is pullulan, it contains, on average, approximately 0.16 sulfate group per monosaccharide, while maintaining its hydrophobic character.

Preferably, when the sulfolipid polysaccharide is Ficoll, it contains, on average, approximately 0.12 sulfate group per monosaccharide, while maintaining its hydrophobic character.

On average, the sulfolipid polysaccharide contains at least 0.01 lipid group per monosaccharide, while maintaining its hydrophobic character. Preferably, the sulfolipid polysaccharide contains, on average, at least 1.05 lipid group per monosaccharide, while maintaining its hydrophobic character.

On average, the sulfolipid polysaccharide contains not more than 2.0 lipid groups per monosaccharide, while maintaining its hydrophobic character. Preferably, the sulfolipid polysaccharide contains, on average, not more than 1.29 lipid groups per monosaccharide, while maintaining its hydrophobic character.

Preferably, when the sulfolipid polysaccharide is maltodextrin, it contains, on average, approximately 1.29 lipid groups per monosaccharide, while maintaining its hydrophobic character.

Preferably, when the sulfolipid polysaccharide is cyclodextrin, it contains, on average, approximately 1.05 lipid groups per monosaccharide, while maintaining its hydrophobic character.

Preferably, when the sulfolipid polysaccharide is insulin, it contains, on average, approximately 1.24 lipid groups per monosaccharide, while maintaining its hydrophobic character.

Preferably, when the sulfolipid polysaccharide is pullulan, it contains, on average, approximately 1.24 lipid groups per monosaccharide, while maintaining its hydrophobic character.

Preferably, when the sulfolipid polysaccharide is Ficoll, it contains, on average, approximately 1.22 lipid groups per monosaccharide, while maintaining its hydrophobic character.

The lipid groups contain, preferably, 4–22 carbon atoms.

The ratio of the sulfate groups to the lipid groups is advantageously 0.01–2 sulfate groups per lipid groups. Preferably, the ratio of the sulfate groups to the lipid groups is 0.10–0.19 sulfate group per lipid group, while maintaining the hydrophobic character of the compound.

Preferably, when the sulfolipid polysaccharide is maltodextrin, the ratio of the sulfate groups to the lipid groups is approximately 0.18 sulfate group per lipid group, while maintaining its hydrophobic character.

Preferably, when the sulfolipid polysaccharide is cyclodextrin, the ratio of the sulfate groups to the lipid groups is approximately 0.19 sulfate group per lipid group, while maintaining its hydrophobic character.

Preferably, when the sulfolipid polysaccharide is insulin, the ratio of the sulfate groups to the lipid groups is approximately 0.15 sulfate group per lipid group, while maintaining its hydrophobic character.

Preferably, when the sulfolipid polysaccharide is pullulan, the ratio of the sulfate groups to the lipid groups is approximately 0.13 sulfate group per lipid group, while maintaining its hydrophobic character.

Preferably, when the sulfolipid polysaccharide is Ficoll, the ratio of the sulfate groups to the lipid groups is approximately 0.10 sulfate group per lipid group, while maintaining its hydrophobic character.

The expression "interface-forming constituent" (or "IFC") denotes a substance which forms, in an aqueous medium, a physical interface between the substance and the aqueous phase.

The interface-forming constituent is selected from the group consisting of a water-immiscible liquid (for example: squalane, soybean oil, mineral oil, hexadecane) or a solid which is insoluble in the aqueous phase.

The insoluble solids in the aqueous phase of the present invention comprise insoluble salts (for example, $Al(OH)_3$, $AlPO_4$, alum, calcium oxalate), microparticles, nanoparticles, microspheres and nanospheres of one or more polymers, copolymers (for example, polyacrylate, poly (methyl methacrylate), polycyanoacrylate, polylactide, polyglycolide), or lipid bi-layers or lipophilic agents (for example, phospholipids) or micelles of surfactants.

Preferably, the "IFC" component is a water-immiscible liquid.

Advantageously, the interface-forming constituent is selected from the group consisting of soybean oil, squalane and hexadecane.

The stable adjuvants for vaccines are those which comprise a (hydrophobic) derivative of a sulfolipid polysaccharide, an interface-forming constituent and an emulsifier.

In addition, the efficacy of the adjuvants according to the present invention is comparable or even greater than that of the standard adjuvants. The local toxicity, that is the reactogenicity of the adjuvants according to the present invention is, in general, less than that of the standard adjuvants and less than that of the adjuvants based on Ficoll.

It would seem that the sulfolipid polysaccharides with a relatively lower molecular weight have a reduced local toxicity.

According to another aspect of the present invention, it is proposed to use sulfolipid polysaccharide as an adjuvant in vaccines.

According to yet another aspect of the present invention, a method is proposed to prepare a vaccine in an emulsion, which is characterized in that an aqueous solution of an antigen is emulsified in the presence of a sulfolipid polysaccharide, an emulsifier and an interface-forming constituent.

According to another aspect of the present invention, a vaccine is proposed which comprises an immunogenic quantity of an antigen (immunogen) and an adjuvant according to the present invention.

Preferably, the concentration of adjuvants is 0.1–100 mg/mL, preferably 2–20 mg/mL.

The vaccine comprises, besides the adjuvant, antigens, for example, of inactivated virus, live virus, bacteria, a subunit, protein, peptide and inactivated influenza virus of strain MRC-11, ovalbumin (OVA), inactivated influenza virus of strain A/Swine and/or inactivated pseudorabies virus (iPRV).

The measured antibody titers were higher than those obtained by the emulsions of mineral oil in water used in commercial products. It has been shown that there is a strong synergistic activity between the SL-Ficoll and the emulsions, which is more pronounced in pigs than in mice (Hilgers et al., Vaccine, Vol. 12, pp. 661–664, 1994). The antibody response in mice was increased significantly (Hilgers et al., Vaccine, Vol. 12, pp. 653–660, 1994).

The conclusion is drawn that the reactogenicity depends on the type of polysaccharide and oil included in the formulations, and that the molecular weight of the polysaccharide is one of the important factors.

The cyclodextrins and their derivatives are well known for their capacity to form inclusion complexes that enclose other substances, such as, for example, substances of pharmaceutical interest, in the hollow formed by their cyclic structure.

The advantages offered by these inclusion complexes include improvement of the solubility, of the bioavailability and/or the chemical stability, increase in length of the half-life, decrease of the secondary effects as well as certain advantages during production, such as the easier obtention of a dry powder to be used as a starting point for liquid preparations.

The sulfolipid polysaccharides (SLP) based on cyclodextrin can thus have interesting applications in addition to their use as adjuvant, which is described above.

Indeed, the SL-cyclodextrins are surfactants because of the simultaneous presence in these molecules of anionic groups (sulfates) and hydrophobic groups (aliphatic chains). This property is at the origin of the formation of micelles in an aqueous phase or mixed micelles in the presence of other surfactants, as well as the formation of emulsions of water-immiscible liquids, suspensions in an aqueous phase of insoluble particles or the formation of interfaces between an aqueous phase and a liquid or solid insoluble substance.

Thus, the SL-cyclodextrins present the double advantage of being able to form inclusion complexes and of being surfactants.

They can thus be considered to form a family of products presenting novel properties which lend themselves to original applications in the pharmaceutical field.

Numerous different SL-cyclodextrins have been obtained; they differ in their physicochemical properties resulting from the type of cyclodextrin (for example, α, β, γ), the content of sulfate groups as well as the content and the nature of the lipid groups.

EXAMPLE 1

Different polysaccharides have been tested to determine their solubility in the organic solvents used for the synthesis, and those with insufficient solubility were abandoned. 4.5 g of maltodextrin (maltodextrin 15; Amylum, Belgium), 4.5 g of β-cyclodextrin (ACROS), 4.5 g of insulin (Dahlia Tubers; Sigma, U.S.A.) and 4.5 g of pullulan (Hayashibara Co. Ltd., Japan) were separately dissolved in mixtures (100 mL) of anhydrous dimethylformamide and anhydrous pyridine (volume ratio 1:1). For a short period of time (48 h), the solutions of these polysaccharides were dried by means of a molecular mesh (size 2 Å) (Merck, Darmstadt, Germany). 6.6 g of lauroyl chloride (Merck, Germany) were added, and the mixtures were incubated for 6 h at 60° C. and for 18 h at room temperature (approximately 15–22° C). Then, 0.6 g of chlorosulfonic acid (Merck, Germany) in a mixture of (10 mL) of anhydrous dimethylformamide and anhydrous pyridine was added, and the incubation procedure at room temperature was repeated. The solvents were removed by evaporation at reduced pressure (200 mb) for 1–2 h at 60° C., and dialyzed using a regenerated cellulose membrane having a cut-off threshold of 10,000 D (SPECTRA/POR) using an isotonic phosphate-buffered saline solution (this saline PBS solution comprises, per liter of water, 8 g of sodium chloride, 0.2 g of potassium chloride and 1.15 g of hydrogenated disodium phosphate having a pH of 7.3) and, subsequently, using ultrapure water until no trace of solvent is detected in the filtrate. The ratio by volume between the dialysis solution (PBS saline solution or ultrapure water) and the residue used during the dialysis is maintained above 10:1 (vol/vol). Dialysis is carried out for at least 10 days, the dialysis solution being replaced at least once per day. The sulfolipid polysaccharides (SLP) so obtained were lyophilized at room temperature, with an internal pressure of less than 0.1 mb and a cold trap at a temperature of less than −25° C.

The composition of the SLP was determined by assaying the polysaccharide, the bound sulfates, the total lipids content and the content of bound lipids, as described above (Vaccine, Vol. 12, pp. 653–660).

The solutions of 1 wt %/volume (wt/vol) of SLP in a phosphate-buffered saline solution (PBS) containing 2% volume/volume (vol/vol) of Tween 80 were prepared by first dissolving the SLP in a minimal volume (20 mL) of methylt-butyl ether (Merck), by adding 2 mL of Tween 80 (Merck) per gram of SLP and by evaporating the methylt-butyl ether at high temperature (±60° C.) and at reduced pressure (50 mb) until a viscous solution of SLP in Tween 80 was obtained. Ten milliliters of water per gram of SLP were slowly added and, then, the appropriate volumes of PBS and of oil were added. The mixture was emulsified using a microfluidizer (Microfluidics Corp., Newton, U.S.A.) until no drop of oil larger than 2 or 3 μm is visible under the microscope (1000×magnification). The emulsions were stored at 4° C. until used.

The vaccines were prepared by mixing one volume of antigen with one volume of adjuvant. The antigens were prepared as described above (Vaccine, Vol. 12, pp. 653–660 and Vaccine, Vol. 12, pp. 661–665). Two solutions of different antigens were used: solution II comprises per milliliter: 10 μg of inactivated influenza virus strain MRC-11 (SOLVAY DUPHAR)+1000 μg OVA (SIGMA); and solution-I comprises per milliliter: 4.4 μg/mL of inactivated influenza virus strain A/Swine (SOLVAY DUPHAR), 4.0 μg of inactivated influenza virus of strain MRC-11 (SOLVAY DUPHAR), 2.0 μg of inactivated influenza virus of strain X-79 (SOLVAY DUPHAR) and $10^8$ $TCID_{50}$ of inactivated pseudorabies virus (iPRV) (SOLVAY DUPHAR).

Female NMRI mice (Charles River, Germany), aged 8–10 weeks (approximately 20 g), were immunized by injection in the paw with 0.025 mL of vaccine and the antibody titers were measured three weeks later.

The antibody titers were expressed as geometric means ($^2$log+SEM). The analysis of the antibody titers was carried out by standardized tests, and the criteria for validity have been described earlier (Vaccine, Vol. 12, pp. 653–660).

Students t-tests were carried out to analyze the statistical significance of the results, and $p<0.05$ was considered to be significant.

Formulations of adjuvants were tested in two independent experiments on mice.

TABLE I

The adjuvant effect of certain emulsions based on sulfolipid polysaccharides (SLP) in oil and in water (SLP/O/W) in mice

| | | | 2 $^2$log du titre d'anticorps contre | | | |
|---|---|---|---|---|---|---|
| 1 Adjuvant | | | MRC 11 | | OVA | |
| [mg SLP et μl huile]/ml | | n | 3 moyenne | SEM | 3 moyenne | SEM |
| 4 Experience I | | | | | | |
| | SL-Maldex15/S/W [10/100] | 6 | 13.1 | 0.7 | 7.3 | 0.2 |
| | SL-Cyclodex./S/W [10/100] | 6 | 12.9 | 1.0 | 7.2 | 0.6 |
| 5 | SL-Inuline/S/W [10/100] | 6 | 12.7 | 0.8 | 7.2 | 0.2 |
| 6 | SL-Pulluane/S/W [10/100] | 6 | 13.3 | 0.7 | 6.9 | 0.4 |
| 7 | SL-Maldex15/soja/W [10/100] | 6 | 12.8 | 0.6 | 6.5 | 0.7 |
| 8 | SL-Cyclodex./soja/W [10/100] | 6 | 13.6 | 1.1 | 6.0 | 0.8 |

TABLE I-continued

The adjuvant effect of certain emulsions based on sulfolipid polysaccharides (SLP) in oil and in water (SLP/O/W) in mice

| | | | 2 ²log du titre d'anticorps contre | | | |
|---|---|---|---|---|---|---|
| 1 Adjuvant | | | MRC 11 | | OVA | |
| [mg SLP et µl huile]/ml | | n | 3 moyenne | SEM | 3 moyenne | SEM |
| 9 | SL-Inuline/soja/W [10/100] | 6 | 12.5 | 0.6 | 6.8 | 1.3 |
| 10 | SL-Pullulane/soja/W [10/100] | 6 | 12.5 | 0.8 | 6.6 | 0.4 |
| | SL-Ficoll/S/W [10/100] | 6 | 13.0 | 0.9 | 6.9 | 0.4 |
| 11 | SL-Ficoll/soja/W [10/100] | 6 | 12.0 | 0.6 | 6.6 | 0.3 |
| 12 | SL-Ficoll/hexadéc./W [10/100] | 4 | 12.4 | 0.9 | 7.2 | 0.6 |
| 13 | SL-Ficoll/h. minérale/W [10/100] | 4 | 12.2 | 0.5 | 6.8 | 0.3 |
| 14 | Contrôle (sans adjuvant) | 6 | 11.3 | 0.7 | 3.5 | 2.0 |
| 15 | Experience II | | | | | |
| | SL-Maldex15/S/W (10/100] | 6 | 13.3 | 0.8 | 9.0 | 1.1 |
| | SL-Cyclodex./S/W [10/100] | 6 | 13.0 | 0.6 | 8.6 | 0.8 |
| 5 | SL-Inuline/S/W [10/100] | 6 | 12.8 | 0.9 | 8.6 | 0.8 |
| 6 | SL-Pullulane/S/W [10/100] | 6 | 13.6 | 0.5 | 8.8 | 0.8 |
| 7 | SL-Maldex15/soja/W [10/100] | 6 | 11.2 | 0.7 | 7.4 | 0.3 |
| 8 | SL-Cyclodex./soja/W [10/100] | 6 | 11.7 | 0.5 | 6.5 | 1.0 |
| 9 | SL-Inuline/soja/W[10/100] | 6 | 11.8 | 0.5 | 7.5 | 0.4 |
| 10 | SL-Pulluiane/soja/W [10/100] | 6 | 10.9 | 0.8 | 7.3 | 0.4 |
| 16 | SL-Maldex15/hexadéc./W [10/100] | 6 | 12.2 | 0.7 | 8.3 | 0.8 |
| 17 | SL-Cyclodex./hexadéc/W [10/100] | 6 | 12.5 | 0.6 | 8.2 | 0.6 |
| 18 | SL-Inuline/hexadéc./W [10/100] | 6 | 12.2 | 0.4 | 7.4 | 0.4 |
| 19 | SL-Pullulane/hexadéc/W [10/100] | 6 | 13.2 | 0.4 | 7.7 | 0.2 |
| 14 | Contrôle (sans adjuvant) | 6 | 10.0 | 0.4 | 4.2 | 0.9 |
| | SL-Ficoll/S/W [10/100] | 2 | 13.4 | 0.7 | 8.5 | 0.7 | n = number of animals
SEM = standard error from mean
Maldex15 = maltodextrin15
Cyclodex. = cyclodextrin
W = water
soy = soybean oil
hexadec. = hexadecane
mineral oil = mineral oil
S = squalane
Key:
1 Adjuvant (mg SLP and µL oil) /mL
2 ²log of the titer of antibodies against
3 Mean
4 Experiment I
5 SL-Inulin/S/W
6 SL-Pullulan/S/W
7 SL-Maldex15/soy/W
8 SL-Cyclodex./soy/W
9 SL-Inulin/soy/W
10 SL-Pullulan/soy/W
11 SL-Ficoll/soy/W
12 SL-Ficoll/hexadec./W
13 SL-Ficoll/mineral oil/W
14 Control (without adjuvant)
15 Experiment II
16 SL-Maldex15/hexadec./W
17 SL-Cyclodex./hexadec./W
18 SL-Inulin/hexadec./W
19 SL-Pullulan/hexadec./W All the SLP/oil/water emulsions increased the humoral response against the influenza virus of strain MRC-11 and against OVA. It has been shown that differences exist as far as the adjuvant effect is concerned between the different formulations, and some caused activities equal to [that of] SL-Ficoll/S/W. No clear effect due to the type of SLP could be observed. With regard to the type of oil used, emulsions comprising squalane (S) produced significantly higher responses than emulsions containing hexadecane, whereas soybean oil caused the least high responses.

EXAMPLE 2

Pigs, aged 8–10 weeks, were tested to detect any presence of antibodies against the viral antigens in question, and animals with detectable antibody titers were excluded.

An emulsion of mineral oil in water, sold under the name SUVAXYN O/W EMULSION (SOLVAY DUPHAR) as well as formulations of SLP in an emulsion of squalane in water were prepared according to the method described in Example 1.

Vaccines containing the formulations with adjuvant were prepared according to the method described in Example 1.

Formulations of SLP/squalane/water were tested to determine their adjuvant effect on pigs with iPRV and inactivated influenza virus—strains MRC-11 and A/Swine, as antigens (Table II). The animals were immunized two times (weeks 0 and 3) and the antibody titers were measured three weeks (week 6) after the second injection.

The titers of antibody against PRV (anti-PRV) were increased by the SL-Ficoll/squalane/water, SL-maltodextrin15/squalane/water, SL-insulin/squalane/water and SL-cyclodextrin/squalane/water emulsions. The measured antibody titers were comparable or higher than those obtained by the emulsions of mineral oil in water used in commercial products. The antibody response against A/Swine was also increased by different SLP/squalane/water formulations, but certain responses were as high as those obtained by the standard oil/water emulsions. The titers of antibodies against MRC-11 were increased by different formulations and some SLP/squalane/water emulsions produced titers comparable to or higher than those obtained with the mineral oil/water emulsions.

The results of these analyses are listed in Table II.

TABLE II

Effect of different sulfolipid polysaccharides combined with serveral oil-in-water emulsions on the anti-iPRV/A/swine/MRC-11 antibody response, measured in pigs

|  | 2 $^2$log des titres d'anticorps à 6 semaines | | | | | |
|---|---|---|---|---|---|---|
| 1 Adjuvant | iPRV | | A/Swine | | MRC-11 | |
| [mg SLP + µl huile]/ml | 3 moyen. | SEM | 3 moyen. | SEM | 3 moyen. | SEM |
| PBS | 0.5 | 0.0 | <3.3 | 0.0 | <3.9 | 0.5 |
| 4 huile minérale/W [0/500] | 6.5 | 0.4 | 10.7 | 1.3 | 10.7 | 0.9 |
| SL-Ficoll/S/W [10/100] | 7.8 | 0.8 | 11.5 | 2.9 | >12.7 | 2.4 |
| SL-Maldex15/S/W [10/100] | 7.5 | 1.1 | 8.7 | 1.1 | 13.1 | 1.3 |
| SL-Cyclodex./S/W[l0/100] | 9.0 | 1.1 | 10.1 | 1.5 | >12.9 | 2.2 |
| 5 SL-Inuline/S/W [10/100] | 8.9 | 1.3 | 10.3 | 1.0 | >13.7 | 1.3 |

SEM = standard deviation from the mean
Maldex15 = maltodextrin15
Cyclodex. = cyclodextrin
S = squalane
W = water
Key:
1 Adjuvant (mg SLP + µL oil)/mL
2 $^2$log of the antibody titers after 6 weeks
3 Mean
4 Mineral oil/W
5 SL-Inulin/S/W From the preceding experiments to test the adjuvant effect simultaneously on two animal species, it has been shown that there is a strong synergistic activity between the SL-Ficolls and the emulsions, and that the synergistic activity is more pronounced in pigs than in mice (Vaccine, Vol. 12, pp. 653–660, 1994; Vaccine, Vol. 12, pp. 661–664, 1994). The antibody response in mice was increased significantly, and it has been shown that there is a pronounced effect of the type of oil used, but not of the type of polysaccharide.

The factor of increase in comparison with animals which did not receive the antigen was limited to one or two $^2$log units in mice. In pigs, the adjuvant effect was more pronounced, primarily because the response against the antigens without adjuvant was very low. The anti-iPRV and anti-A/Swine and anti-MRC-11 antibody titers were increased by more than six $^2$log units.

The adjuvants based on mineral oil increase the antibody response significantly, but different novel formulations of adjuvants caused even higher titers. The SL-Ficoll/S/W adjuvant presented above (Vaccine, Vol. 12, pp. 653–660 and Vaccine, Vol. 12, pp. 661–665) was shown to be more effective than mineral oil, while some novel SLP have exerted an activity equal to or greater than the SL-Ficoll.

EXAMPLE 3

Besides the adjuvant effect, other properties are of importance in evaluating a vaccine. They include the local reaction, which is an important aspect, although a certain level of reaction at the site of injection is in general accepted by certain animal species. The local toxicity was tested in vivo by monitoring the swelling of the paws of mice after injection of the vaccine. It has been shown that this method is very sensitive.

The formulations of SLP in an emulsion of squalane in water, of soybean oil in water, mineral oil and hexadecane in water, and a control without adjuvant were prepared according to the method described in Example 1.

Vaccines containing the formulations with adjuvant were prepared according to the method described in Example 1.

Groups of six mice were treated with 25 µL of vaccine by subcutaneous injection in the sole of the back left foot. The vaccine comprised a solution of antigens containing 10 µg of MRC-11 and 1 mg of ovalbumin (OVA) per milliliter of PBS and one volume of adjuvant.

The thickness of the paws was measured one day before and at several intervals after the injection using a semielectronic apparatus especially developed for this purpose by the State University of Utrecht in the Netherlands. The precision of this apparatus is approximately 0.02 mm.

The swelling was calculated by subtracting the thickness of the paw before treatment from the thickness of the paw after treatment, and it is expressed in 0.01 mm.

The results of these experiments are listed in Table III.

TABLE III

Reactogenicity of different adjuvants in mice
Experiment I

| 1 Adjuvant [mg SLP + µl huile]ml | 2 gonflement moyen (10⁻²mm) 3 Jours | | | | | | | | |
|---|---|---|---|---|---|---|---|---|---|
| | 1 | 2 | 3 | 4 | 7 | 11 | 14 | 18 | 25 |
| SL-Maldex15/S/W [10/100] | 169 | 110 | 89 | 65 | 39 | 16 | 18 | 19 | 17 |
| SL-Cyclodex./S/W [10/100] | 88 | 21 | 8 | 8 | 9 | 3 | 6 | 12 | −1 |
| 4 SL-Inuline/S/W [10/100] | 146 | 145 | 94 | 102 | 44 | 30 | 25 | 26 | 20 |
| SL-Pullulane/S/W [10/100] | 235 | 231 | 137 | 112 | 87 | 74 | 60 | 64 | 42 |
| SL-Maldex15/soja/W [10/100] | 30 | 10 | 5 | 0 | 2 | 10 | 5 | 5 | 1 |
| 6 SL-Cyclodex./soja/W [10/100] | 2 | 0 | 0 | 0 | 0 | 0 | 4 | 10 | −7 |
| 7 SL-Inuline/soja/W [10/100] | 117 | 64 | 13 | 7 | 7 | 10 | 20 | 18 | 1 |
| 8 SL-Pullulane/soja/W [10/100] | 40 | 23 | 7 | 0 | 0 | 0 | 3 | 10 | −2 |
| SL-Ficoll/S/W [10/100] | 196 | 273 | 299 | 305 | 305 | 237 | 177 | 144 | 97 |
| 9 SL-Ficoll/soja/W [10/100] | 124 | 59 | 24 | 20 | 26 | 17 | 12 | 7 | −5 |
| 10 SL-Ficoll/hexadéc./W [10/100] | 241 | 277 | 242 | 209 | 92 | 35 | 42 | 49 | 14 |
| 11 SL-Ficoll/h. minérale/W [10/100] | 233 | 295 | 300 | 292 | 201 | 165 | 120 | 89 | 75 |
| 12 Contrôle (sans adjuvant) | 2 | 0 | 0 | 0 | 0 | 0 | 4 | −6 | −4 |

Maldex15 = maltodextrin15
Cyclodex. = cyclodextrin
soy = soybean oil
W = water
hexadec. = hexadecane
mineral oil = mineral oil
S = squalane
Key:
1 Adjuvant (mg SLP + µL oil)/mL
2 Mean swelling
3 Days
4 SL-Inulin/S/W
4a SL-Pullulan/S/W
5 SL-Maldex15/soy/W
6 SL-Cyclodex./soy/W
7 SL-Inulin/soy/W
8 SL-Pullulan/soy/W
9 SL-Ficoll/soy/W
10 SL-Ficoll/hexadec./W
11 SL-Ficoll/mineral oil/W
12 Control (without adjuvant)

Experiment II

| 1 Adjuvant [mg SLP + µl huile]ml | 2 gonflement moyen (10⁻² mm) 3 Jours | | | | | |
|---|---|---|---|---|---|---|
| | 1 | 2 | 6 | 10 | 17 | 22 |
| SL-Maldex15/S/W [10/100] | 133 | 95 | 61 | 30 | 35 | 24 |
| SL-Cyclodex./S/W [10/100] | 62 | 54 | 10 | 15 | 17 | 1 |
| 4 SL-Inuline/S/W [10/100] | 176 | 134 | 71 | 51 | 55 | 48 |
| 4a SL-Pullulane/S/W [10/100] | 200 | 199 | 91 | 94 | 77 | 46 |
| 5 SL-Maldex15/soja/W [10/100] | 20 | 10 | 7 | 0 | 0 | 0 |
| 6 SL-Cyclodex./soja/W [10/100] | 19 | 16 | 21 | 16 | 11 | 12 |
| 7 SL-Induline/soja/W [10/100] | 52 | 38 | 22 | 11 | 24 | 0 |
| 8 SL-Pullane/soja/W [10/100] | 52 | 38 | 11 | 4 | 15 | 0 |
| 9 SL-/Maldex15/hexadene/W [10/100] | 108 | 65 | 14 | 14 | 22 | 0 |
| 10 SL-Cyclodex./hexadec./W [10/100] | 107 | 74 | 14 | 10 | 25 | 0 |
| 11 SL-Inuline/hexadéc./W [10/100] | 121 | 114 | 46 | 30 | 22 | 0 |

-continued

Experiment II

| 1 Adjuvant | 2 gonflement moyen ($10^{-2}$ mm) 3 Jours | | | | | |
|---|---|---|---|---|---|---|
| [mg SLP + µl huile]ml | 1 | 2 | 6 | 10 | 17 | 22 |
| 12 SL-Pullulane/hexadéc./W [10/100] | 224 | 213 | 112 | 59 | 40 | 23 |
| 13 Controle (sans adjuvant) | 2 | 0 | 0 | 0 | 0 | 0 |
| SL-Ficoll/S/W [10/100] | 73 | 293 | 325 | 239 | 178 | 99 |

Maldex15 = maltodextrin15
Cyclodex. = cyclodextrin
hexadec. = hexadecane
soy = soybean oil
S = squalane
W = water
Key:
1 Adjuvant (mg SLP + µL oil)/mL
2 Mean swelling
3 Days
4 SL-Inulin/S/W
4a SL-Pullulan/S/W
5 SL-Maldex15/soy/W
6 SL-Cyclodex./soy/W
7 SL-Inulin/soy/W
8 SL-Pullulan/soy/W
9 SL-Maldex15/hexadec.
10 SL-Cyclodex./hexadec./W
11 SL-Inulin/hexadec./W
12 SL-Pullulan/hexadec./W
13 Control (without adjuvant)

The formulations cause different degrees of swelling at the injection site, and the swelling, which was very strong in some cases during the first days, slowly disappeared (Table III). The emulsions comprising hexadecane generally caused stronger reactions than those containing soybean oil. With regard to the SLP, the emulsions of squalane comprising SL-Ficoll caused stronger swellings, which were maintained for more than three weeks. The emulsions containing SL-maltodextrin15, SL-insulin or SL-pullulan caused considerable swelling reactions which, however, disappeared more rapidly than those caused by the SL-Ficoll, and they persisted only for one to two weeks.

The reactogenicity of SL-cyclodextrin included in different oils was very weak or even absent. Emulsions containing SL-cyclodextrin in squalane or hexadecane caused some swellings for one or two days after the injection, whereas the SL-cyclodextrin in soybean oil caused no visible response.

The reactogenicity, that is the local toxicity, which was tested on mice, revealed pronounced effects as a function of the type of oil and the type of polysaccharide. In general, the SL-Ficoll caused stronger reactions than the other SLP tested. The SL-Ficoll, combined with either squalane or mineral oil, caused a very strong and persistent local reaction, whereas the SL-Ficoll combined with hexadecane and soybean oil produced only moderate or weaker reactions, respectively (Table II). The emulsions based on squalane caused significantly stronger reactions than those comprising hexadecane. Soybean oil caused only very weak reactions.

The hydrophobic character of these oils is different. Squalane, mineral oil and hexadecane are strongly hydrophobic hydrocarbons, whereas soybean oil, being a mixture of different substances, is less hydrophobic. The hydrophobic character of different oils is illustrated by the HLB value of the detergents required to obtain stable emulsion in water.

SL-Pullulan caused stronger local toxicities than the three other SLP. SL-Insulin and SL-maltodextrin15 caused considerable local swellings, whereas SL-cyclodextrin caused a notable reaction only for one or two days.

Among the other characteristics, the SLP differ in their molecular weight which decreases from SL-Ficoll=to that of SL-pullulan>SL-insulin>SL-maltodextrin15>SL-cyclodextrin. A parallelism between the reactogenicity and the molecular weight can be observed, but other studies need to be conducted to establish a direct relation.

From the above it was concluded that the reactogenicity depends on the type of polysaccharide and oil included in the formulation and that the molecular weight of the polysaccharide is an important factor.

EXAMPLE 4

Sulfolipid derivatives of maltodextrin15, insulin, cyclodextrin and pullulan were synthesized and incorporated in oil-in-water emulsions based on squalane, mineral oil, hexadecane and soybean oil, and the stability was studied in vitro.

The SLPs of the present invention were synthesized according to the method described in Example 1 and mixed in oil-in-water emulsions of squalane, hexadecane and soybean oil, and the stability of those emulsions were studied in vitro.

The formulations of SLP in an emulsion of squalane in water, soybean oil in water and hexadecane in water were prepared according to the method described in Example 1.

The stability of the emulsions was tested by exposing the formulations to a high temperature for a certain period of time. In general, the emulsions are less stable at high temperature, and the test at higher temperature was considered to give indications on the long-term behavior at lower temperature.

The stability of the emulsions was determined at 37° C. Sterile aliquots of 5 mL of emulsion were incubated at 37° C., and the formation of oil droplets, the appearance of an oily phase and other modifications were verified each day inspection of the emulsions with the naked eye.

The SLP with a ratio S/L of approximately 0.1/1.0 were incorporated in emulsions of the oil-in-water type based on squalane, hexadecane and soybean oil.

Sterile aliquots comprising 0.01% (wt/vol) of thimerosal (SIGMA) were incubated at 37° C., and the state of the emulsions was established at different time intervals inspection with the naked eye.

The results of these experiments are listed in Table IV.

TABLE IV

Stability of different emulsions of different oils comprising SLP at a final concentration of 1% (wt/vol) SLP, 2% (vol/vol) Tween 80, 10% (v/v) of oil in PBS

| 1 Adjuvant [mg SLP + μl huile]/ml | 2 Stabilité à 37° C. au jour: | | | | | | | | | | |
|---|---|---|---|---|---|---|---|---|---|---|---|
| | 1 | 2 | 7 | 10 | 14 | 21 | 28 | 35 | 46 | 53 | 115 |
| SL-Maldex15/S/W [10/100] | + | + | + | + | + | + | + | + | + | + | ±/+ |
| SL-Cyclodex./S/W [10/100] | + | + | + | + | + | + | + | + | + | + | ±/+ |
| 3 SL-Inuline/S/W [10/100] | + | + | + | + | + | + | ± | ± | + | + | + |
| 3a SL-Pullulane/S/W [10/100] | + | + | + | + | + | + | + | + | ± | − | − |
| 4 SL-Maldex15/soja/W [10/100] | + | + | + | + | + | + | + | + | + | + | + |
| 5 SL-Cyclodex./soja/W [10/100] | + | + | + | + | + | + | + | + | + | + | + |
| 6 SL-Inuline/soja/W [10/100] | + | + | + | + | + | + | + | + | + | + | + |
| 7 SL-Pullulane/soja/W [10/100] | + | + | + | + | + | + | + | + | + | + | − |
| 8 SL-Maldex15/hexadéc./W [10/100] | + | + | + | + | + | + | + | + | + | + | + |
| 9 SL-Cyclodex./hexadéc./W [10/100] | + | + | + | + | + | + | + | + | + | + | ± |
| 10 SL-Inuline/hexadéc./W [10/100] | + | + | + | + | + | + | + | + | + | + | ± |
| 11 SL-Pullulane/hexadéc./W [10/100] | + | + | + | + | + | + | + | + | + | + | − |

Maldex15 = Maltodextrin 15
Cyclodex. = cyclodextrin
soy = soybean oil
hexadec. = hexadecane
S = squalane
W = water The new SLP (SL-pullulan, SL-insulin, SL-maltodextrin15 and SL-cyclodextrin) incorporated in these emulsions of squalane oil, hexadecane or soybean oil have a remarkable stability. The emulsions of SL-insulin, SL-cyclodextrin and SL-maltodextrin15 in squalane remain stable for more than 53 days at 37° C. This is considered to be a great improvement in comparison with the emulsions of SL-Ficoll/squalane/water. In spite of the limited predictive value of the stability test at 37° C., it shows an increased resistance against destabilization factors.

All the emulsions, with the exception of SL-pullulan/squalane/water remained stable for at least 53 days at 37° C. After 115 days, most of the emulsions comprising SL-maltodextrin15, SL-cyclodextrin and SL-insulin remain stable, although emulsions with squalane and hexadecane showed a few oil droplets on the emulsion.

What is claimed is:

1. Adjuvant for vaccines comprising a sulfolipid polysaccharide combined with an interface-forming constituent characterized in that the sulfolipid polysaccharide is a hydrophobic polysaccharide which is selected from the group consisting of cyclodextrin, maltodextrin, insulin, and pullulan.

2. Adjuvant according to claim 1, characterized in that the sulfolipid polysaccharide is a cyclodextrin.

3. Adjuvant according to claim 1, wherein the sulfolipid polysaccharide is selected from the group consisting of α-cyclodextrin, β-cyclodextrin and γ-cyclodextrin.

4. Adjuvant according to claim 1, characterized in that the sulfolipid polysaccharide contains, on average, at least 0.01 sulfate group per monosaccharide, while maintaining its hydrophobic character.

5. Adjuvant according to claim 4, characterized in that the sulfolipid polysaccharide contains, on average, at least 0.12 sulfate group per monosaccharide, while maintaining its hydrophobic character.

6. Adjuvant according to claim 1, characterized in that the sulfolipid polysaccharide contains, on average, not more than 1.0 sulfate group per monosaccharide, while maintaining its hydrophobic character.

7. Adjuvant according to claim 6, characterized in that the sulfolipid polysaccharide contains, on average, not more than 0.23 sulfate group per monosaccharide, while maintaining its hydrophobic character.

8. Adjuvant according to claim 1, characterized in that the sulfolipid polysaccharide is maltodextrin and it contains, on average, 0.23 sulfate group per monosaccharide, while maintaining its hydrophobic character.

9. Adjuvant according to claim 1, characterized in that the sulfolipid polysaccharide is cyclodextrin and it contains, on average, 0.20 sulfate group per monosaccharide, while maintaining its hydrophobic character.

10. Adjuvant according to claim 1, characterized in that the sulfolipid polysaccharide is insulin and it contains, on average, 0.19 sulfate group per monosaccharide, while maintaining its hydrophobic character.

11. Adjuvant according to claim 1, characterized in that the sulfolipid polysaccharide is pullulan and it contains, on average, 0.16 sulfate group per monosaccharide, while maintaining its hydrophobic character.

12. Adjuvant according to claim 1, characterized in that the sulfolipid polysaccharide contains, on average, at least 0.01 lipid group per monosaccharide, while maintaining its hydrophobic character.

13. Adjuvant according to claim 12, characterized in that the sulfolipid polysaccharide contains, on average, at least 1.05 lipid groups per monosaccharide, while maintaining its hydrophobic character.

14. Adjuvant according to claim 1, characterized in that the sulfolipid polysaccharide, on average, does not contain more than 2.0 lipid groups per monosaccharide, while maintaining its hydrophobic character.

15. Adjuvant according to claim 14, characterized in that the sulfolipid polysaccharide, on average, does not contain more than 1.29 lipid groups per monosaccharide, while maintaining its hydrophobic character.

16. Adjuvant according to claim 1, characterized in that the sulfolipid polysaccharide is maltodextrin containing, on average, 1.29 lipid groups per monosaccharide, while maintaining its hydrophobic character.

17. Adjuvant according to claim 1, characterized in that the sulfolipid polysaccharide is cyclodextrin containing, on average, 1.05 lipid groups per monosaccharide, while maintaining its hydrophobic character.

18. Adjuvant according to claim 1, characterized in that the sulfolipid polysaccharide is insulin containing, on average, 1.24 lipid groups per monosaccharide, while maintaining its hydrophobic character.

19. Adjuvant according to claim 1, characterized in that the sulfolipid polysaccharide is pullulan containing, on average, 1.24 lipid groups per monosaccharide, while maintaining its hydrophobic character.

20. Adjuvant according to claim 1, characterized in that the lipid groups comprise 4–22 carbon atoms.

21. Adjuvant according to claim 1, characterized in that the ratio of sulfate groups to lipid groups is 0.01–2 sulfate groups per lipid group, while maintaining the hydrophobic character of the compound.

22. Adjuvant according to claim 21, characterized in that the ratio of sulfate groups to lipid groups is 0.10–0.19 sulfate group per lipid group, while maintaining the hydrophobic character of the compound.

23. Adjuvant according to claim 1, characterized in that the sulfolipid polysaccharide is maltodextrin containing a ratio of sulfate groups to lipid groups of approximately 0.18 sulfate group per lipid group, while maintaining its hydrophobic character.

24. Adjuvant according to claim 1, characterized in that the sulfolipid polysaccharide is cyclodextrin containing a ratio of sulfate groups to lipid groups of approximately 0.19 sulfate group per lipid group, while maintaining its hydrophobic character.

25. Adjuvant according to claim 1, characterized in that the sulfolipid polysaccharide is insulin containing a ratio of sulfate groups to lipid groups of approximately 0.15 sulfate group per lipid group, while maintaining its hydrophobic character.

26. Adjuvant according to claim 1, characterized in that the sulfolipid polysaccharide is pullulan containing a ratio of sulfate groups to lipid groups of approximately 0.13 sulfate group per lipid group, while maintaining its hydrophobic character.

27. Adjuvant according to claim 1, characterized in that the interface-forming constituent is selected from the group consisting of a water-immiscible liquid and a solid which is insoluble in the aqueous phase.

28. Adjuvant according to claim 27, characterized in that the water-immiscible liquid is selected from the group consisting of squlane, soybean oil, mineral oil and hexadecane.

29. Adjuvant according to claim 1, wherein the concentration of sulfolipid polysaccharide is 0.1–100 mg/mL.

30. Adjuvant according to claim 29, wherein the concentration of sulfolipid polysaccharide is 2–20 mg/mL.

31. Process for the preparation of a vaccine in an emulsion, characterized in that an aqueous solution of an antigen, a sulfolipid polysaccharide and interface-forming component according to claim 1, and an emulsifier are emulsified.

32. Vaccine comprising an immunogenic quantity of an antigen and an adjuvant comprising a sulfolipid polysaccharide and an interface-forming constituent according to claim 1.

33. A method for reducing the toxicity of an oil-in-water or water-in-oil vaccine which comprises adding a hydrophobic sulfolipid polysaccharide which is selected from the group consisting of cyclodextrin, maltodextrin, insulin and pullulan.

* * * * *

UNITED STATES PATENT AND TRADEMARK OFFICE
CERTIFICATE OF CORRECTION

PATENT NO.    : 6,328,965 B1
DATED         : December 11, 2001
INVENTOR(S)   : Luuk Hilgers It is certified that error appears in the above-identified patent and that said Letters Patent is hereby corrected as shown below:

Column 2,
Lines 31 and 56, the word "insulin", each occurrence, should read -- inulin --.

Column 3,
Lines 19 and 44, the word "insulin", each occurrence, should read -- inulin --.

Column 5,
Line 24, the word "insulin", should read -- inulin --.

Column 9,
Line 3, the word "insulin", should read -- inulin --.

Column 13,
Line 40, the word "insulin", should read -- inulin --.

Column 14,
Lines 2, 8 and 24, the word "insulin", each occurrence, should read -- inulin --.
Lines 37, 40 and 50, the word "insulin", each occurrence, should read -- inulin --.

Column 15,
Line 57, "insulin" should read -- inulin --.

UNITED STATES PATENT AND TRADEMARK OFFICE
CERTIFICATE OF CORRECTION

PATENT NO. : 6,328,965 B1
DATED : December 11, 2001
INVENTOR(S) : Luuk Hilgers

It is certified that error appears in the above-identified patent and that said Letters Patent is hereby corrected as shown below:

Column 16,
Line 58, "insulin" should read -- inulin --.

Column 17,
Line 22, "insulin" should read -- inulin --.

Column 18,
Line 7, "insulin" should read -- inulin --.
Line 41, "insulin" should read -- inulin --.

Signed and Sealed this

Thirty-first Day of December, 2002

JAMES E. ROGAN
*Director of the United States Patent and Trademark Office*